(12) United States Patent
Baranova et al.

(10) Patent No.: US 8,222,220 B2
(45) Date of Patent: Jul. 17, 2012

(54) NANOGENOMICS FOR MEDICINE: SIRNA ENGINEERING

(75) Inventors: Ancha V. Baranova, Annadale, VA (US); Amanda C. Zirzow, Falls Church, VA (US)

(73) Assignee: George Mason Intellectual Properties, Inc., Fairfax, VA (US)

( * ) Notice: Subject to any disclaimer, the term of this patent is extended or adjusted under 35 U.S.C. 154(b) by 161 days.

(21) Appl. No.: 12/453,477

(22) Filed: May 12, 2009

(65) Prior Publication Data

US 2009/0306185 A1 Dec. 10, 2009

Related U.S. Application Data

(60) Provisional application No. 61/052,837, filed on May 13, 2008.

(51) Int. Cl.
*A61K 48/00* (2006.01)
*C07H 21/04* (2006.01)
*C07H 21/02* (2006.01)
*C12N 15/85* (2006.01)

(52) U.S. Cl. ......... 514/44; 536/23.1; 536/24.5; 435/325

(58) Field of Classification Search .................. None
See application file for complete search history.

(56) References Cited

U.S. PATENT DOCUMENTS

2009/0148535 A1* 6/2009 Bamdad ..................... 424/499
2009/0226528 A1* 9/2009 Czech et al. ................ 424/491

OTHER PUBLICATIONS

Chono et al., An efficient and low immunostimulatory nanoparticle formulation for systemic siRNA delivery to the tumor, Journal of Controlled Release, vol. 131, Issue 1, Oct. 6, 2008, pp. 64-69.*
Blessing, et al. "Monomolecular collapse of plasmid DNA into stable virus-like particles," *Proc. Natl. Acad. Sci.* USA. 1998, vol. 95, pp. 1427-1431.
Li, et al. "Tumor-targeted Delivery of siRNA by Self-assembled Nanoparticles," *Molecular Therapy.* 2008, vol. 16 No. 1, pp. 163-169.

* cited by examiner

*Primary Examiner* — Amy Bowman
(74) *Attorney, Agent, or Firm* — Foley & Lardner LLP

(57) ABSTRACT

Described herein are materials and methods for the delivery of siRNA and the production of nanoparticles useful for the delivery of siRNA. Methods of treating a disease or disorder using the nanoparticles described herein also are disclosed.

14 Claims, 22 Drawing Sheets

NANOGENOMICS FOR MEDICINE: SIRNA ENGINEERING

INFORMATION ON RELATED APPLICATIONS

This application claims the benefit of U.S. Provisional Application 61/052,837, filed May 13, 2008, the entire contents of which are herein by reference.

BACKGROUND

Control of gene expression in a sequence-specific manner by silencing with small interfering RNA (siRNA) in living cells holds great promise both as a novel therapeutic approach and as a new instrument for a drug target discovery. Cellular and animal models demonstrate the potential application of siRNA-based therapies for cancer, viral infections and inflammatory diseases. The advancement of siRNA-based therapeutics into the clinic is hampered by two significant obstacles. One obstacle takes the form of non-specific, that is "off-target," binding of siRNAs to unintended mRNAs. Such non-specific binding that leads to partial or complete silencing accompanied by unwanted cytotoxic effects. Another obstacle is the lack of the means for the targeted delivery of a stable siRNA into a diseased tissue (e.g., tumor), but not into the adjacent normal cells or connected organs. Thus, improvements in siRNA engineering and delivery are needed to realize the potential of siRNA-based therapies.

SUMMARY

In one aspect, nanoparticles are provided comprising: a) one or more DNA polymers; and b) one or more siRNA molecules. In a particular embodiment, the nanoparticle further comprises protein, e.g., bovine serum albumin. In a particular embodiment, the one or more DNA polymers is herring sperm DNA, salmon sperm DNA or Derinat. In a particular embodiment, the nanoparticle comprises a double-stranded RNA. In a particular embodiment, the double-stranded RNA is a siRNA selected to specifically hybridize to a transcript expressed from a target gene. In a particular embodiment, the nanoparticle comprises a targeting molecule attached to the DNA polymer. In a particular embodiment, the targeting molecule is an antibody or fragment thereof, or an aptamer.

Methods also are provided for using the nanoparticles and compositions described herein to deliver siRNA to a desired tissue or in methods for treating gene expression diseases or disorders.

In another aspect, methods are provided for delivering a siRNA to a subject comprising administering the siRNA to the subject, wherein the siRNA is contained in a DNA nanoparticle. In one embodiment, the DNA nanoparticle comprises protein, such as bovine serum albumin. In another embodiment, the DNA nanoparticle comprises one or more DNA polymers derived from herring sperm DNA, salmon sperm DNA or Derinat. In another embodiment, the DNA nanoparticle comprises a targeting molecule. In one example, the targeting molecule is an antibody or fragment thereof, or an aptamer.

Methods also are provided for making a protein DNA nanoparticle, comprising: a) concentrating a mixture of protein and DNA; and b) reconstituting the concentrated protein and DNA mixture in a suitable buffer. In a particular embodiment, the protein and DNA mixture is concentrated at a ratio of about 4:1 protein:DNA (w/w). In one embodiment, the resulting nanoparticles have a mean diameter of about 104.3 nm. In other examples, the resulting nanoparticles have a mean diameters of about 1243.5 nm, 64.7 nm or 19.2 nm. In another embodiment, the concentrated protein and DNA mixture is reconstituted in 1×PBS or water. In one aspect, the DNA in the protein and DNA mixture is attached to a targeting molecule. In a particular embodiment, the methods further comprise attaching a targeting molecule to the DNA of the formed nanoparticle after concentrating the protein and DNA mixture.

In another aspect, methods are provided for identifying a siRNA sequence that will selectively silence a target gene, comprising selecting a siRNA from a set of sequences wherein each sequence in the set is unique with regard to a given transcriptome, and wherein the sequence is selected based on its ability to anneal to a transcript from a desired target gene.

In another embodiment, methods are provided for treating a disorder, comprising administering a DNA nanoparticle comprising a siRNA molecule that silences the expression of a target gene that causes the disorder, thereby treating the disorder. In one embodiment, the nanoparticle further comprises a protein, such as bovine serum albumin. In another aspect, the nanoparticle comprises DNA from the group consisting of: one or more DNA polymers is herring sperm DNA, salmon sperm DNA or Derinat. The nanoparticle can comprise a double-stranded RNA. In another embodiment, the nanoparticle comprises a targeting molecule attached to the DNA polymer. In a particular embodiment, the targeting molecule is an antibody or fragment thereof, or an aptamer.

Other objects, features and advantages will become apparent from the following detailed description. The detailed description and specific examples are given for illustration only since various changes and modifications within the spirit and scope of the invention will become apparent to those skilled in the art from this detailed description. Further, the examples demonstrate the principle of the invention and cannot be expected to specifically illustrate the application of this invention to all the examples where it will be obviously useful to those skilled in the prior art.

BRIEF DESCRIPTION OF THE DRAWINGS

FIG. 4A: Mean diameter (53.8±25.74 nm) of herring DNA concentrated with 11.1 mg/mL BSA. FIG. 4B: Mean diameter (19.2±5.71 nm) of herring DNA concentrated with 5.56 mg/mL BSA. FIG. 4C: Mean diameter (271.2±250.02 nm) of herring DNA concentrated with 2.78 mg/mL BSA. FIG. 4D: Mean diameter (336.2±394.45 nm) of herring DNA concentrated with 1.39 mg/mL BSA. FIG. 4E: Mean diameter (1476.0±62.39 nm) of herring DNA (not concentrated).

FIG. 5A: Mean diameter (30.0±10.44 nm) of herring DNA concentrated with 11.1 mg/mL BSA. FIG. 5B: Mean diameter (22.1±2.66 nm) of herring DNA concentrated with 5.56 mg/mL BSA. FIG. 5C: Mean diameter (466.6±383.79 nm) of herring DNA concentrated with 2.78 mg/mL BSA. FIG. 5D: Mean diameter (129.5±72.48 nm) of herring DNA concentrated with 1.39 mg/mL BSA. FIG. 5E: Mean diameter (412.6±243.22 nm) of herring DNA concentrated with 0.69 mg/mL BSA. FIG. 5F: Mean diameter (603.8±298.68 nm) of herring DNA concentrated with 0.345 mg/mL BSA.

FIG. 6A: Mean diameter (12.5±0.63 nm) of Derinat DNA concentrated with 11.1 mg/mL BSA. FIG. 6B: Mean diameter (28.7±18.31 nm) of Derinat DNA concentrated with 5.56 mg/mL BSA. FIG. 6C: Mean diameter (154.0±164.08 nm) of Derinat DNA concentrated with 1.39 mg/mL BSA. FIG. 6D: Mean diameter (762.4±7.26 FIGS. nm) of Derinat DNA without BSA (reconstituted in water at 25°).

FIG. 7A: concentrated with 100 µL of BSA (11.1 mg/mL), reconstituted with water (mean diameter of nanoparticles: 104.3±2.20 nm). FIG. 7B: concentrated overnight, reconstituted with 100 µL of BSA (11.1 mg/mL) (mean diameter of nanoparticles: 1243.5±1370.56 nm).

FIG. 8A: concentrated with 100 µL of BSA (11.1 mg/mL), reconstituted by vortexing in 1×PBS (mean diameter of nanoparticles: 64.7±54.00 mm). FIG. 8B: concentrated with 100 µL of BSA (11.1 mg/mL), reconstituted by pipetting in 1×PBS (mean diameter of nanoparticles: 19.2±5.71 nm).

DETAILED DESCRIPTION

Figure 1:
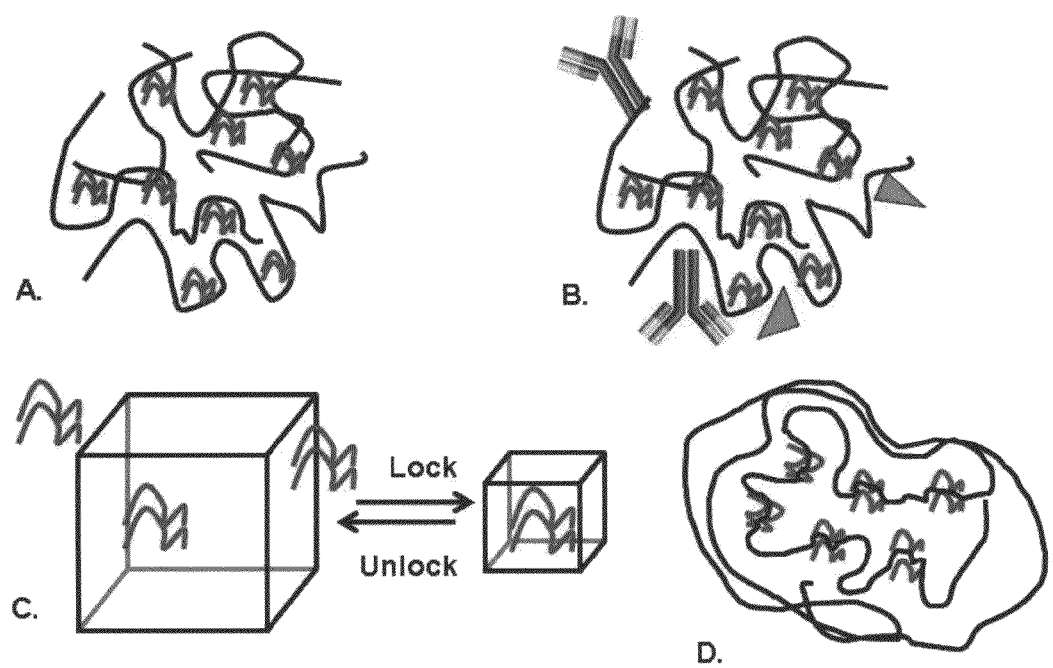
FIG. 1 is a schematic representation of DNA nanoparticles for siRNA delivery. Single- or double-stranded DNA is shown in black, double-stranded siRNA in green. Panel A: Simplest implementation of the biodegradable DNA nanoparticle slowing down the kinetics of the degradation of siRNA. Panel B: Targeting of the DNA nanoparticle to the tissue of interest can be achieved by the crosslinking of DNA with various proteins and protein fragments that specifically bind to surface receptors of the target cells. Panel C: Branched DNA structures stably locked at physiological temperatures are sterically capable of encapsulating siRNA molecules. Panel D: Parts of the DNA molecules within DNA-siRNA nanoparticles can be engineered to form dsRNA-DNA triplexes.

Described herein are methods for identifying siRNA sequences, methods for isolating stabilized siRNA formulations, and methods and compositions for making and using siRNA formulations.

Definitions

As used herein, the term "small interfering RNA" refers to a class of about 18-25 nucleotide-long double-stranded RNA molecules (e.g., about 21 nt in length). The average length of standard siRNA molecules is 21 or 23 nt. siRNA plays a variety of roles in biology. Described herein are composition, methods and methods for delivery of siRNA useful for RNA interference (RNAi) to specifically down regulate gene expression of a desired target gene. Although the mechanism of RNAi involves a double-stranded RNA molecule, single-stranded or partially double-stranded RNA molecules can be delivered to a desired tissue, whereupon the single-stranded or partially double-stranded RNA molecules are converted to a desired double-stranded RNA molecule that down-regulates target gene expression.

As used herein, the term "specific" where used in combination with, for example, "binding" or "hybridization," refers to binding or hybridization to a target sequence without appreciable binding to non-target sequence(s). One of skill in the art would know how to set parameters such that "specific binding" is physiologically meaningful. For gene silencing using siRNA, for example, specific annealing of an siRNA to a target gene results in effective silencing of the target gene, without producing unwanted levels of unwanted silencing due to off-target hybridization of the siRNA to non-target gene transcripts.

As used herein, the term "nucleic acid" refers to deoxyribonucleotides or ribonucleotides and polymers thereof in either single- or double-stranded form. The term encompasses a nucleic acid containing known nucleotide analogs or modified backbone residues or linkages, which are synthetic, naturally-occurring, and non-naturally occurring, which have similar binding properties as the reference nucleic acids, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). A nucleic acid sequence also encompasses naturally-occurring allelic variants of said nucleic acid.

As used herein, the term "oligonucleotide" refers to a nucleic acid molecule consisting of two or more deoxyribonucleotides or ribonucleotides joined by phosphodiester bonds, and preferably containing between about 6 and about 300 nucleotides in length. The size of the oligonucleotide will depend on many factors, including the ultimate function or use of the oligonucleotide. Preferably, an oligonucleotide that functions as an extension primer or probe will be sufficiently long to prime the synthesis of extension products in the presence of a catalyst, e.g., DNA polymerase, and deoxynucleotide triphosphates. As used herein, the term "oligonucleotide" further refers to an oligonucleotide that has been modified structurally ("modified oligonucleotide") but functions similarly to the unmodified oligonucleotide. A modified oligonucleotide can contain non-naturally occurring portions, such as, for example, altered sugar moieties or inter-sugar linkages, such as a phosphorothioate.

As used herein, the term "gene" refers to a nucleic acid sequence that encodes and regulates expression of a polypeptide. A gene includes, therefore, regulatory elements, e.g., promoters, splice sites, enhancers, repressor binding sites, etc. A gene can have many different "alleles," which are sequence variations that can affect the polypeptide sequence or expression level, or have no effect on the polypeptide. A gene can include one or more "open reading frames," which are nucleic acid sequences that encode a contiguous polypeptide. A gene can be present either endogenously or exogenously.

As used herein, the term "efficacy" refers to the degree to which a desired effect is obtained. An "effective amount" is an amount sufficient to obtain the desired effect (one of skill in the art would be able to determine an effective amount based on known assays, clinical procedures and the methods and compositions described herein). The nanoparticles described herein are, for example, configured to release a therapeutically effective amount of an agent for treating, for example, myocardial infarction or ischemia. The methods described herein, therefore, enhance the delivery and uptake of siRNA molecules into a specific, desired tissue, wherein the siRNA function of the particular molecule allows for the down-regulation of a desired gene product, thereby effectively treating a disease associated with the gene product. An effective amount of a particular siRNA is sufficient to produce a clinically-relevant down-regulation of a particular gene, as determined by one of skill in the art. As used herein, the term "effective amount" refers a dosage of siRNA necessary to achieve a desired effect, e.g., the down-regulation of a specific gene target to the degree to which a desired effect is obtained. The term "effective amount" also refers to relief or reduction of one or more symptoms or clinical events associated with ocular disease.

As used herein, "a significant change in the expression level" or "silencing" refers to a decrease of the expression product of a target gene. An expression product can be any downstream product derived from the gene, including, for example, a transcription product or a subsequent translation product. The term refers to a change by at least about 10%, about 20%, about 25%, about 30%, at least about 40%, about 50%, at least about 60%, about 70%, or about 90%, about 100%, about 150%, or about 200%, or greater.

For the purposes of the compositions and methods described herein, the siRNA is between about 15 to about 30 nucleotides in length, e.g., between 21 to 23 nucleotides in length. The siRNA molecule can be fully double-stranded, partially double-stranded, or single-stranded, as one of skill in the art would be able to generate molecules that either start out as double-stranded RNA molecules, or would be converted to double-stranded RNA molecules in vivo after uptake into a desired tissue or cell.

The siRNA described herein are encapsulated in the form of a nanoparticle. As used herein, the term "nanoparticle" is meant to describe a particle having a submicron dimension. The dimension can be measured across the largest portion of the particle. The dimension can be a length, width or diameter of the particle.

As used herein, the term "antibody" refers to an intact antibody or an antigen binding fragment ("binding moiety") or single chain (e.g., light or heavy chain) thereof. An intact antibody is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The variable regions of the heavy and light chains contain a binding domain that interacts with an antigen.

As used herein, "binding moiety" refers to one or more fragments of an intact antibody that retain the ability to specifically bind to a given antigen. Antigen binding functions of an antibody can be performed by fragments of an intact antibody. Although the two domains of the Fv fragment, $V_L$ and $V_H$, are coded for by separate genes, they can be joined, for example, using recombinant methods, e.g., using an artificial peptide linker that enables them to be made as a single protein chain (Bird et al., *Science*, 242:423-426, 1988; Huston et al., *Proc. Natl. Acad. Sci. USA*, 85:5879-5883, 1988). These antibody fragments are obtained using conventional techniques known to those of skill in the art, and the fragments are screened for utility in the same manner as are intact antibodies.

As used herein, "subject," "individual," "animal," "patient" or "mammal" refers to any subject, for example, a mammalian subject, for whom diagnosis, detection, prognosis, or therapy is desired. Mammalian subjects include but are not limited to humans, domestic animals, farm animals, and zoo, sport, or pet animals such as dogs, cattle, swine and other such animals.

As used herein, "transcriptome" refers to the set of all messenger RNA (mRNA) molecules, or "transcripts" produced in one or a population of cells. The term can be applied to the total set of transcripts in a given organism, or to the specific subset of transcripts present in a particular cell type.

I. siRNA Engineering

In one aspect, methods are provided for identifying a siRNA sequence that will selectively silence a target gene, comprising selecting a siRNA from a set of sequences wherein each sequence in the set is unique with regard to a given transcriptome, and wherein the sequence is selected based on its ability to anneal to a transcript from a desired target gene.

siRNA-based silencing of the gene expression involves homology-dependent degradation of cognate mRNA directed by a complex ribonuclease system (Agrawal, N. et al., *Microbiol. Mol. Biol. Rev.*, 67:657-685, 2003). Unwanted annealing of siRNA to unrelated but partially homologous mRNAs dilutes the targeted silencing effect, and, more importantly, causes the degradation of mRNAs from non-targeted genes, thereby producing unwanted, secondary silencing effects, possibly evoking cytotoxicity. A study of different nonsense siRNAs, for example, revealed that even non-specific, scrambled dsRNA affect viability, mitosis and motility of human cells (Tscharganeh, D. et al., *Pathol. Oncol. Res.*, 13:84-90, 2007).

Approaches for the design of therapeutic siRNA typically start with the sequence of the mRNA to be silenced, which is used as a template for detecting 21-mer target sites that conform to various sets of rules that predict effective siRNA target sites (Reynolds, A. et al., *Nat. Biotechnol.*, 22:326-330, 2004; Jagla, B. et al., *RNA*, 11:864-872, 2005). Among the criteria often used for efficient siRNA design are G+C content, presence of internal repeats and the presence of an A/U-rich 5' end. Some researchers also emphasized the importance of certain secondary structures at the siRNA target site (Heale, B. et al., *Nucl. Acids Res.*, 33:e30, 2005 (Erratum in: *Nucl. Acids Res.*, 34:4653) and/or thermodynamics parameters (Shabalina, S. et al., *BMC Bionformatics*, 7:65, 2006). These parameters have led to a number of reliable algorithms for the prediction of highly specific and effective individual siRNAs (Peek, A., *BMC Bionformatics*, 8:182, 2007; Liu, C. et al., *BMC Bioinformatics*, 8:164, 2007.

After the completion of the design stage, which typically generates hundreds of suitable siRNA candidates per gene, some advanced algorithms perform a further selection aimed at elimination of the most obvious off-targets. A typical approach for reduction of the off-target effects involves applying the basic local alignment search tool (BLAST) to organism-specific mRNA databases. BLAST is typically applied with a significant penalty to nucleotide mismatch (e.g., −3), allowing one to choose best-fit siRNA among multiple designed candidates. Answers are promptly returned by the BLAST algorithm, but significant alignments may be missed. On the other hand, an exhaustive Smith-Waterman local alignment algorithm may return accurate answers but is very time consuming to perform. Some authors propose additional indirect measures for mismatch tolerance (Naito, Y. et al., *Nucl. Acids Res.*, 32:W124-129, 2004; Yamada, T. and Morishita, S., Bioinformatics, 21:1316-1324, 2005) or on an absence of the short string matches to the 3' areas of other human genes (Birmingham, A. et al., *Nat. Protoc.*, 2:2068-2078, 2007). Even more cumbersome approaches to eliminate off-target siRNA hybridization, including identification of off-targeted genes via microarray-based gene expression analysis (Anderson, E. et al., *Methods Mol. Biol.*, 442:45-63, 2008; Vankooningsloo, S. et al., *FEBS J.*, 275:2738-2753, 2008), have also been used.

Stretches of sequence of as few as 11 to 15 consecutive nucleotides are enough to produce unwanted silencing (Jackson, A. et al., *Nat. Biotechnol.*, 21:635-637, 2005). While it might not be possible to eliminate off-target siRNA hybridization completely, it is clearly desirable to minimize an interaction of siRNAs with incompletely matching mRNA molecules. To this end, an "inverted" approach to siRNA design that takes as in input the precomputed, minimized transcriptomes that pass a redundancy masking purification procedure, is herein described. An algorithm that allows one to map all unique short-string sequences (hereafter called "targets") that are 9 to 15 nt in size (length "N") within large sets of sequences, e.g., a set of all known transcripts in certain organisms (Alsheddi, T. et al., *Mol. Biol. (Mosk.)*, 42:163-167, 2008), is used. The algorithm ensures the uniqueness of the "target" in the transcriptome of interest. The "target" is considered unique if it is present only in one of the sequences from the study set; otherwise all of the identical short-string sequences including the primary target will be masked. The candidate antisense strand of siRNA is formed by concatenating the unique target with its suffix of length equal to (21 nt). The resulting output file represents a list of the potential siRNA candidates for any given gene in the transcriptome of interest. An exemplary algorithm is the Comprehensive Redundancy Minimizer (CRM). For the human transcriptome, the CRM returns a set of highly specific potential siRNA candidates. The generated database allows retrieval of the precomputed siRNA sets with non-redundant kernels of length 12 to 15 nt for every gene in the human genome.

Another approach to generating a set of unique siRNA target sequences relies on the idea of a tree-based storage and sorting of subsequences that delivers a comprehensive analysis of exact matches within the input data through an exhaustive database search. Each subsequence of a fixed length is stored in a quaternary sort tree. The tree is similar to a binary tree commonly used in computer science and graph theory applications, but instead of two (left and right) pointers at each node it has four pointers associated with the nucleic acids A, C, G, C, so that a sequence represents a unique path from the root to a leaf. Important information about each sequence, such as its frequency, location within the large sequence and other statistics, is stored in each of the leaves making it easy to analyze the results and avoid unnecessary sequence comparisons. The storage space is generated on demand so that no extra space is wasted. This approach is a highly efficient C-based approach that delivers a comprehensive analysis of exact matches within the input data through an exhaustive database search. This search has the ability to find biologically significant features within large gene databases. This algorithm allows for the identification of certain subsequences within a given human gene dataset.

The set of pre-screened targets can be used, for example, as an input for the traditional "set-of-rules" types of siRNA prediction algorithms known in the art. A subsequent application of the "set-of-rules" algorithm(s) to the pre-computed set of unique siRNA targets is beneficial for the therapeutic success. Nevertheless, pre-screening with an algorithm that identifies a unique set of siRNA targets within a transcriptome improves an average efficacy of the designed siRNAs. Analysis of the published sets of siRNAs with known efficacies reveals the positive and significant (p-value=0.0001) correlation between efficacy and presence in CRM-approved set (Saetrom, P and Snove, Jr., O., *Biochem. Biophys. Res. Commun.*, 321:247-253, 2004). Such filtering limits the number of possible siRNA candidates that needs to be analyzed by a "set-of-rules" application(s), thus, increasing the speed of calculations without losing its specificity and selectivity.

Many published siRNAs used in silencing experiments produce off-target annealing that could be prevented by filtering. Less than 15% of surveyed in vitro studies employed siRNA constructs with minimal off-target effects. In many cases, overlooked off-targeting of siRNA may potentially lead to incorrect conclusions, e.g., silencing of Histone Acetyl Transferase Tip60 (HTATIP), which is involved in the p53 response, by siRNA that non-specifically target Cyclin M4, which plays a role in cell cycle regulation (Legube G. et al., *J. Biol. Chem.*, 279:44825-44833, 2004). Pre-screening of transcriptomes with a filtering algorithm can improve both the validity of the functional conclusions made in siRNA knock-out experiments and the specificity of siRNA therapeutics.

One aspect of this approach is the number of candidate siRNA shrink exponentially as the length of the unique overlapping kernel targets comprising siRNA candidate decreases. A pre-computed set of human siRNAs with minimized off-target hybridization comprised of the unique targets with length N=12 covers only 9.4% of the human transcriptome. If the gene to be silenced does not contain a target site allowing for the design of a siRNA with N=12, one would decrease the stringency and look among less desirable siRNA candidates with N=13 covering 71% of the human transcriptome, or even with higher length of the target. The simplification of the human transcriptome by exclusion of genes not identified and characterized by any experimental evidence improves the coverage of the human genes only marginally.

Another improvement for identifying siRNA target sequences is to subdivide the human transcriptome into overlapping sets of the tissue and cell-type specific mRNAs, then perform separate runs of filtering on each set of sequences. In this case, every siRNA is pre-screened to exclude only physiological interactions with off-target mRNAs, e.g., siRNA aimed at the suppression HCV virus replicating in hepatocytes can be pre-selected for minimization of its interactions with mRNAs expressed in human liver, but not in human brain. In this case, the intracellular specificity of siRNA targeting is increased sufficiently, but its therapeutic application mandate the coupling with tissue-specific delivery.

Accordingly, the nucleic acid payload of the nanoparticle, e.g., a siRNA, can be selected using, for example, a filtering algorithm described herein or any algorithm that eliminates all or substantially all off-target binders. Subsequent to this first selection stage, additional selection criteria can be applied to further optimize siRNA sequences, e.g., optimized annealing sequences, optimized structural sequences, optimized annealing energy of sequences, etc.

In some embodiments, the siRNA can be monitored by, for example, attaching moieties to the siRNA strands to allow for monitoring of the double-stranded character of the siRNA molecule. Each strand of a double-stranded siRNA molecule, for example, can be labeled with a fluorophore. The fluorophore of one strand could be on that emits at the excitation wavelength of the fluorophore attached to the complimentary strand. In such a scenario, the second fluorophore will emit at the excitation wavelength of the first fluorophore only when the two siRNA strands are in proximity, e.g., where they are annealed.

II. DNA Nanoparticles

DNA nanoparticles described herein provide a structural delivery vehicle for a nucleic acid therapeutic, e.g., an siRNA. A DNA nanoparticle is a matrix formed by bulk, e.g., non-specific, DNA polymers. The non-specific matrix polymers can be of any sequence. Such polymers can be isolated from natural sources such as salmon sperm, herring sperm, or sturgeon. These sources of DNA provide bulk DNA that contain whole-genomic sequences that are not "target-specific" sequences. The DNA nanoparticles are useful, for example, in carrying siRNA sequences. Although it is possible that some small stretch of non-specific DNA is in fact somewhat homologous to the target siRNA sequence, the vast majority of the DNA polymers used for the basket matrix is non-sequence-specific DNA, unrelated to the siRNA target sequence.

The DNA nanoparticle serves to reduce degradation of the nucleic acid payload by, for example, sterically shielding the nucleic acid payload from cytosolic nucleases, such as RNAses. The DNA nanoparticles also serve as competitive inhibitors of cellular nucleases, thereby further reducing degradation of the nucleic acid payload.

The DNA used for the matrix also can serve as a substrate to which targeting molecules can be attached, e.g., crosslinked. Such targeting molecules can be, for example, antibodies, aptamers, or specific binding domains that bind to surface proteins, e.g., receptors, of desired target cells or cells of certain tissues, e.g., tumor tissues. Examples of such targeting molecules are known in the art. The chemistry of attaching targeting molecules to DNA is known to one of skill in the art. The nanoparticles described herein can be targeted through the attachment of an appropriate targeting molecule to any desired molecule, cell or tissue.

The nanoparticles described herein can be comprised of DNA polymers that are locked into particular conformations that further stabilize its payload. The locked conformations can be reversibly unlocked, e.g., through changes in temperature ort chemical environment, such that release of its nucleic acid payload can be manipulated, e.g., controlled such that release only occurs after the nanoparticle has reached a desired target.

The DNA nanoparticle can be formed by concentrating a DNA polymer and then reconstituting the concentrated polymers with a suitable buffer (e.g., PBS or water). The size, e.g., mean diameter, of the nanoparticles can be controlled by concentrating a mixture of DNA and protein. As the DNA for the matrix is non-specific, the protein that is used to form the nanoparticle is also non-specific. Examples of such proteins include, for example, bovine serum albumin (BSA), gelatin, and milk proteins. Control of the ratio of protein to DNA allows for control of the DNA nanoparticle formed after reconstitution after concentration. Other factors that control DNA nanoparticle size include temperature and chemical environment during concentration and/or reconstitution.

The rate of clearance from circulation has been a constant barrier in developing both naked DNA and naked siRNA therapeutics due to degradation by serum nucleases. The siRNA containing DNA nanoparticles described herein serve as biodegradable "DNA cages" or "DNA baskets" (FIG. 1, Panel A) that provide both the steric separation of siRNA from endonucleases and a local excess of the substrate for endonuclease action, thus, slowing down the kinetics of the degradation of siRNA.

In addition to an increase in a half-life of siRNA, the DNA component of the DNA/siRNA nanoparticle serves as a substrate for the particle targeting modifications (FIG. 1, Panel B), such as crosslinked targeting molecules like antibodies. Thus, the conformational problems arising form the chemical modification of siRNA are eliminated by the placement of these modifications onto expendable DNA component. Targeting the DNA nanoparticle to the tissue of interest can be achieved, for example, by crosslinking the DNA with various proteins and protein fragments that are specific binders of surface receptors of the target cells. Examples of such proteins include, for example, antibodies, scFv antibody fragments, or peptide ligands such as Arg-Gly-Asp (RGD) or Epo peptides (FIG. 1, Panel B).

The chemistry of DNA protein crosslinking in vitro and in situ is known to one of skill in the art. Crosslinking can be performed by a number of techniques including, for example, application of formaldehyde (Wells, J. and Farnham, P., *Methods*, 26:48-56, 2002), glutaraldehyde or other chemical agents. Additionally, DNA-protein crosslinking can be achieved by the use of high energy UV lasers has been developed (Russmann, C. et al., *Methods Mol. Biol.*, 148:611-620, 2001). This approach allows maximization of the yield of crosslinked complexes while the structural damage to DNA and protein components remains minimal.

In other embodiments, the DNA nanoparticle can incorporate branched DNA structures stably "locked" at physiological temperatures. Advances of the structural nanotechnology of DNA allow the construction of mesh-like DNA constructs made up of about 4 strands of about 40 base DNA bricks structurally resembling 4-sticky-end Holliday junctions (Kii, H. et al., *Nanosci. Nanotechnol.*, 7:726-729, 2007) sterically capable of encapsulating siRNA molecules (FIG. 1, Panel C).

In other embodiments, the DNA-siRNA nanoparticles are engineered to form dsRNA-DNA triplexes that have significantly higher formation energy and are therefore much more stable than dsDNA-DNA triplexes (Guga, P. et al., *Biophys. J.*, 92:2507-2515, 2007). Recent experiments demonstrate the ability for non(polyPu·polyPy) sequences to form the Hoogsten bonding with the third polynucleotide strain, eventually forming a triple helix (Kato, M. et al., *Biophys. J.*, 85:402-408, 2003; Kato, M. et al., *Eur. J. Biochem.*, 269: 3632-3636, 2002). The complete DNA sequence of a DNA nanoparticle need not interact with the siRNA molecules (FIG. 1, Panel D), allowing for the addition of relatively large DNA spacers serving as the "ribs" of the DNA matrix or as a substrate for endonuclease degradation.

Embodiments will be further described in the following non-limiting example.

EXAMPLES

Example 1

Tree-Based Algorithm

A tree-based method for filtering duplicate siRNA target sequences within a transcriptome uses indices to store sequence data. Such a method does not require matching or comparing, and, therefore, allows for a faster identification of duplicate sequences. By storing sequence data in data trees, computationally intensive algorithms can be avoided. Examples describing tree-based and other approaches are generally described in, for example Giladi, E. et al., *Bioinformatics*, 18:873-877, 2002; and Ning, Z. et al., *Genome Res.*, 11: 1725-1729, 2001 (the entire contents of each of these publications is herein incorporated by reference).

Memory analysis for such an approach is as follows:

$$M_{TOT} = M_{STOR} + M_{GENE} + M_{DATA} + M_{TREE}$$

Suppose there G genes with average length $\Delta L$
MSTOR=20*G*$\Delta L$
MGENE=16*G
MDATA=G*$\Delta L$
MTREE$\leq$24*($4^{n+1}$)/3

In our database G=18,000 and ΔL=3,000

$$M_{STOR}+M_{GENE}+M_{DATA} \sim 1.1 \text{ gigabytes}$$

Example 2

Stabilized siRNA Formulations

This investigation demonstrates that protein/DNA interactions can be exploited to form DNA nanoparticles with a stable size distribution. This study uses of Derinat (Деринат), a DNA-based immunomodulator approved for human use in Russia, as the primary material for synthesizing the DNA nanoparticles. Centrifugal vacuum concentration (SpeedVac) of DNA and bovine serum albumin (BSA) at specific concentrations can control the mean size distribution of particles in solution. As the protein concentration is increased, the mean size distribution of DNA nanoparticle decreases. A stable mean size distribution of 12.5±0.63 nm has been established for the BSA/Derinat nanoparticle.

To overcome the problems of instability of siRNA in the bloodstream and the targeted delivery of this molecule to the cell of interest, this study uses these BSA/DNA nanoparticles to carry siRNA particles. The siRNA containing BSA/DNA nanoparticles serve as biodegradable "DNA cages" or "DNA baskets" (FIG. 1) that will provide both the steric separation of siRNA from nucleases and the local excess of the substrate for nuclease action, thus, slowing down the rate of the degradation of siRNA.

A 1:100 ratio of siRNA to BSA/DNA nanoparticle is SpeedVac concentrated. The degradation of the siRNA in biologically active media (fetal bovine serum) is studied by FRET analysis. siRNA is protected by BSA/DNA nanoparticle and is degraded by nuclease at a significantly slower rate than naked siRNA.

Materials and Methods

Figure 8A:
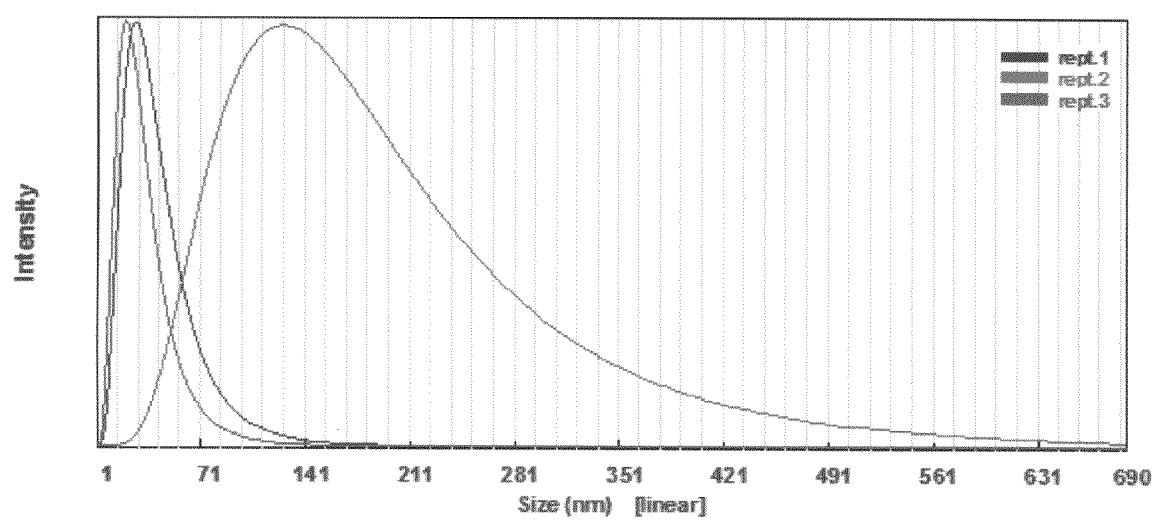
FIGS. 8A and 8B show the mean diameter (nm) of 25 µL herring sperm DNA nanoparticles concentrated overnight (37° C.).
Figure 8B:
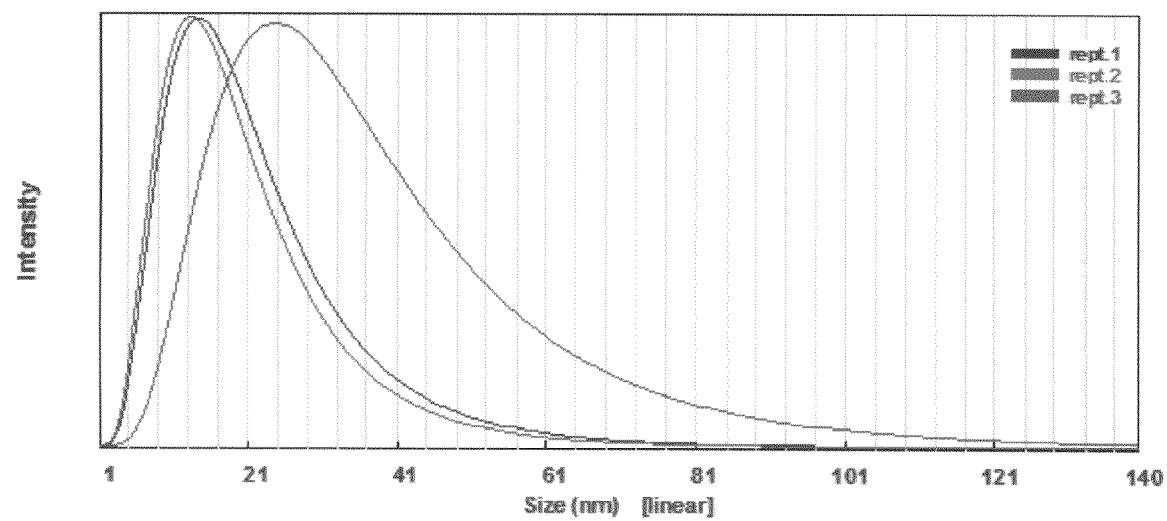

Different sources of DNA, including Sigma herring sperm DNA and Sigma ssDNA were used. To create DNA nanoparticles, DNA and different concentrations (ranging from 11.1 mg/mL to 0.345 mg/mL) of bovine serum albumin (BSA) were concentrated overnight (SpeedVac) and rapidly reconstituted with 1×PBS before determining the mean size distribution (FIGS. 4A-E, 5A-F and 6A-D). Concentrated BSA/DNA nanoparticles were reconstituted by pipette mixing, rather than vortexing. Pipette mixing results in smaller mean diameter sizes of the nanoparticles, along with smaller standard deviations (FIGS. 8A and 8B). Pipette mixing is also important to ensure that the DNA, and more importantly, the siRNA, is not sheared. The size distribution of the nanoparticles was determined by dynamic light scattering techniques.

Figure 7A:
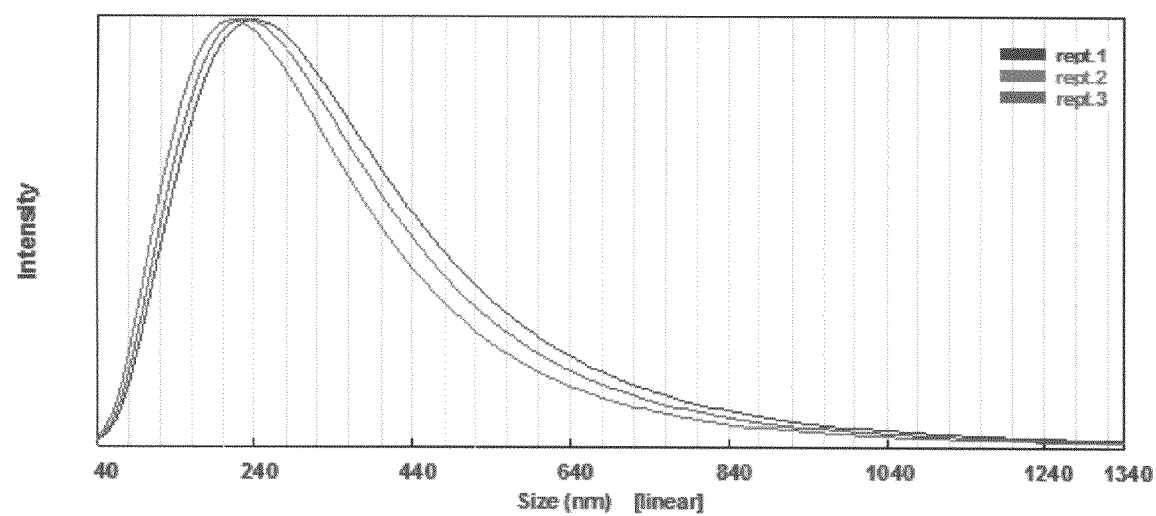
FIGS. 7A and 7B show the mean diameter (nm) of 25 µL herring sperm DNA nanoparticles concentrated overnight (25° C.).
Figure 7B:
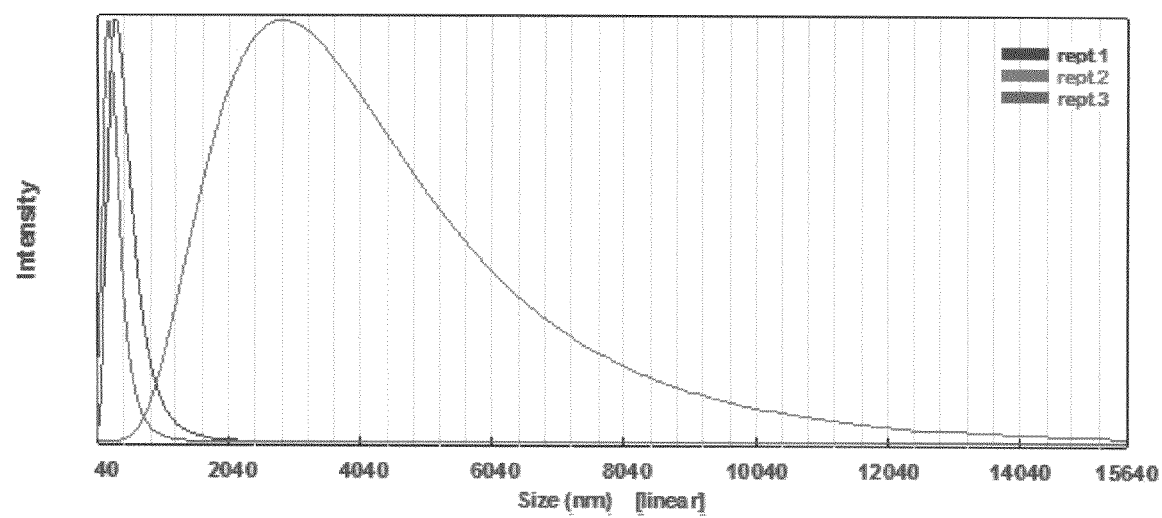

To determine if SpeedVac concentration is necessary for the formation of DNA/BSA nanoparticle, 25 µL of Sigma herring sperm DNA was aliquoted into two Eppendorf tubes. To one of these tubes, 100 µL BSA (11.1 mg/mL) was added, and the same amount of molecular grade water was added to the other tube. The results show that centrifugal vacuum concentration is necessary for DNA/protein interactions to for a stable mean size distribution (FIGS. 7A and 7B).

A stable mean size distribution of 12.5±0.63 nm for BSA/DNA nanoparticles was a result of the formulation of 25 µL of Derinat (5 mg/mL) and 500 µL BSA (11.1 mg/mL). siRNA-containing DNA nanoparticles are created by rapid concentration of siRNA, DNA and BSA via SpeedVac. The concentrated DNA nanoparticles are reconstituted with 1×PBS or molecular grade water for use.

siRNA degradation is quantified in a series of experiments involving profiling of degradation kinetics of siRNA protected by a DNA nanoparticle versus naked siRNA in the same type of the solution (e.g., containing RNAse). Fluorescently labeled siRNA (SEQ ID NOS:1 and 2) includes a quencher, thereby assuring that the fluorescence of the solution is proportional to the degradation of siRNA. Kinetics of siRNA degradation is profiled by measuring the fluorescence of the solution containing siRNA protected by the DNA nanoparticle and naked siRNA after 1 min, 3 min, 5 min, 10 min, 15 min, 30 min, 1 hr, 2 hrs and 5 hrs after adding siRNA to fetal bovine serum. Additional factors, including, for example, temperature (within physiological limitations), ratio of DNA to siRNA and size of DNA/RNA particles, also are examined.

```
5' --UUG UCUAA CCCUA ACUGA GTT 3'    (SEQ ID NO: 1)

3' TTAAC AGAUU GGGAU UGACU C 5'      (SEQ ID NO: 2)
```

The siRNA represented by complementary sequences SEQ ID NOS:1 and 2 has been shown to silence GFP expression with high efficiency. A fluorophore and quencher are bound to this molecule to facilitate analysis of degradation via fluorometric assays.

Results

Figure 2:
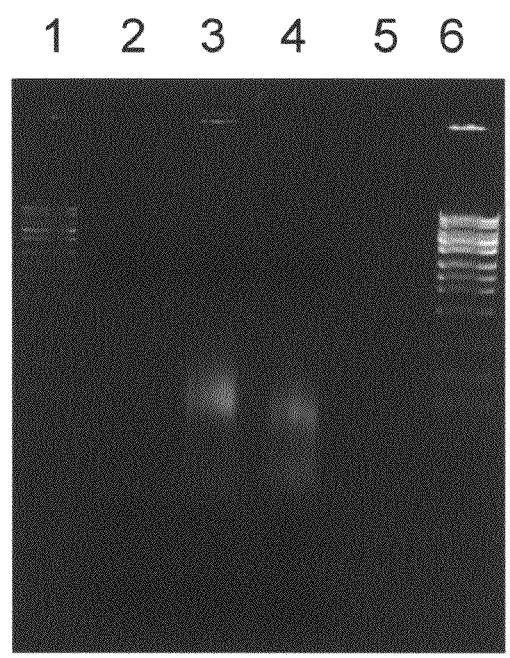
FIG. 2 is a stained gel showing characteristics ssDNA derived from herring sperm and Derinat. Lane 1: 0.25×exACTGene 1 kb ladder; Lane 2: ssDNA; Lane 3: herring sperm DNA; Lane 4: Derinat; Lane 5: empty; Lane 6: 1×exACTGene 1 kb ladder.
Figure 3:
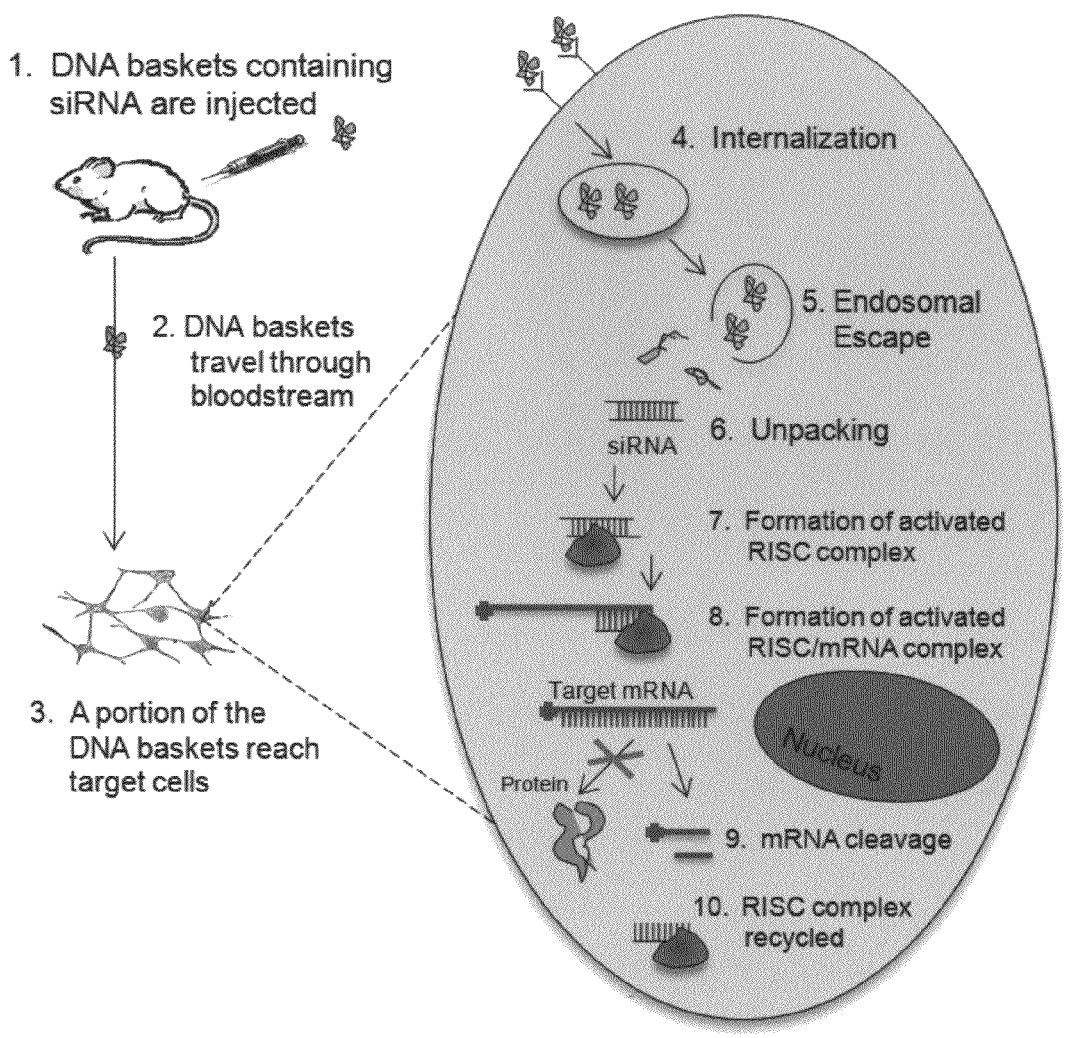
FIG. 3 is a schematic representation of the formation of DNA nanoparticles and their subsequent use for in vivo delivery of a siRNA nucleic acid.
Figure 4A:
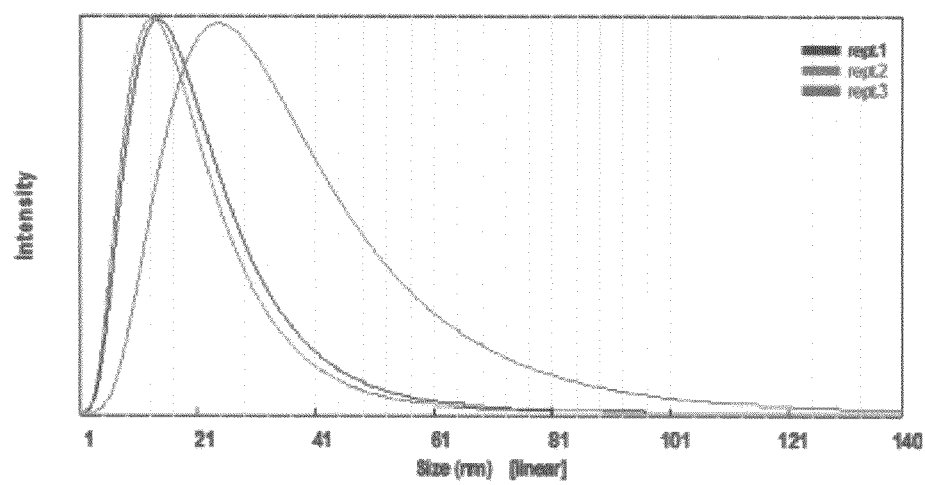
FIGS. 4A through 4E show the mean diameter (nm) of 25 μL herring DNA nanoparticles concentrated overnight with 500 μL of various concentrations of BSA, reconstituted with 1×PBS (37° C.).
Figure 4B:
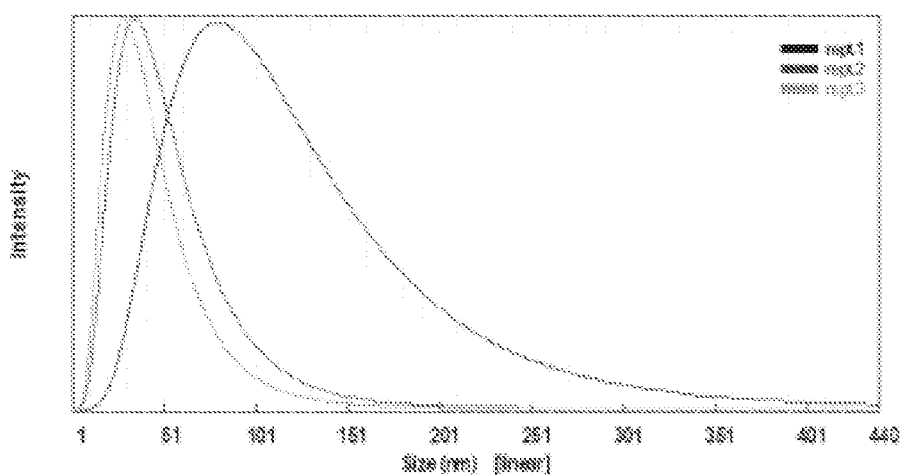
Figure 4C:
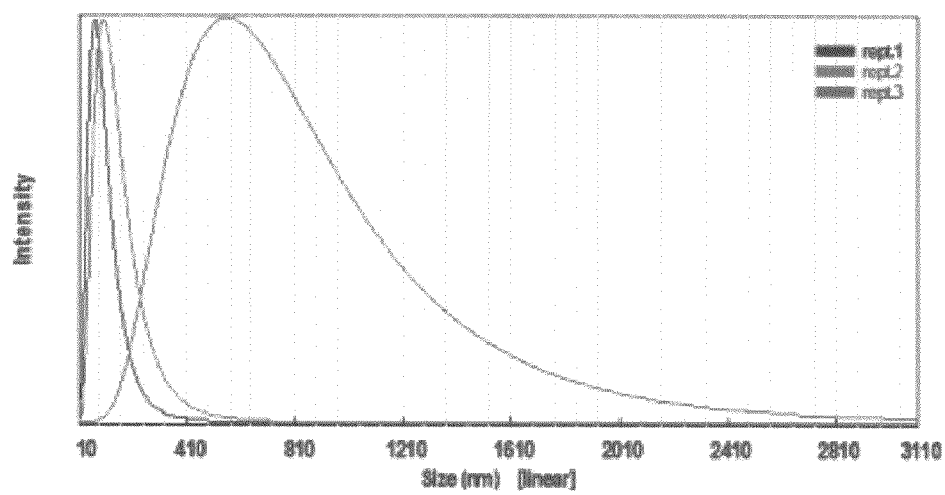
Figure 4D:
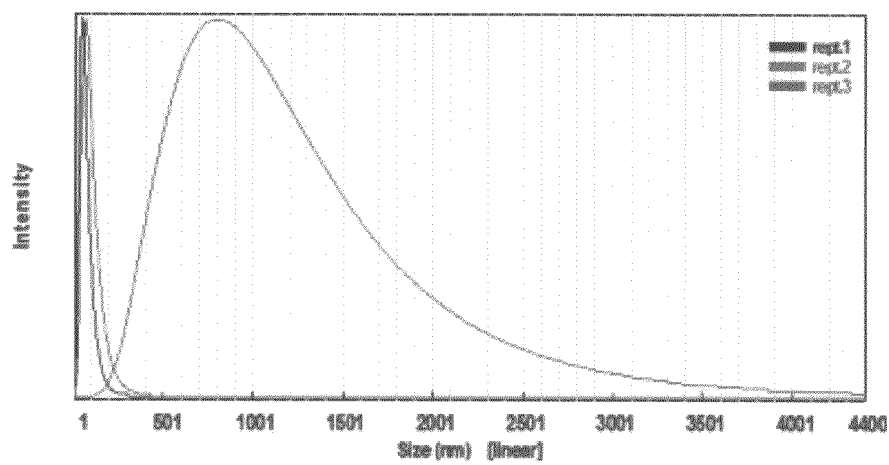
Figure 4E:
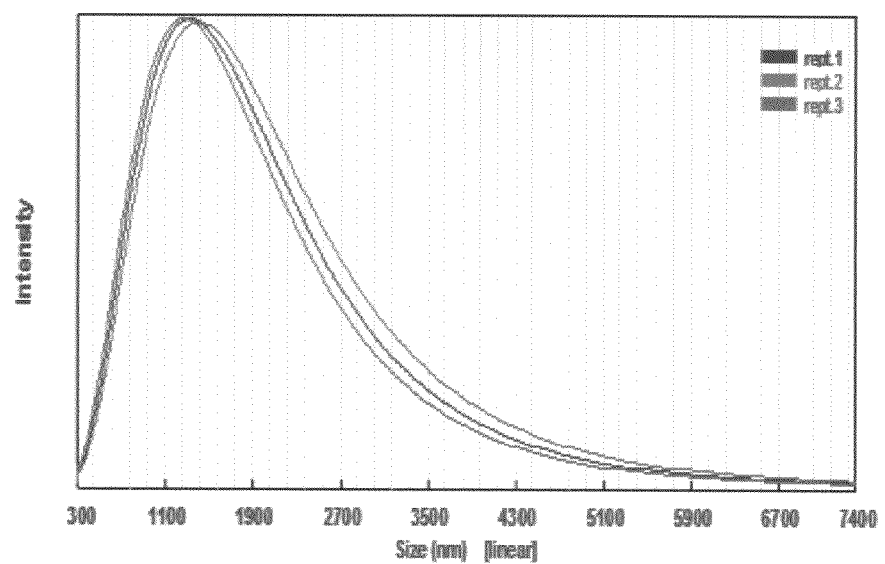
Figure 5A:
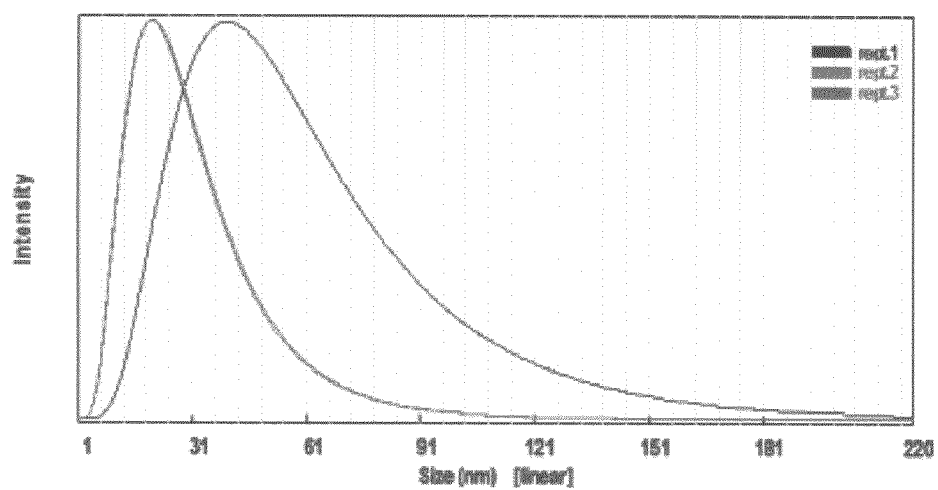
FIGS. 5A through 5F show the mean diameter (nm) of 25 µL herring DNA nanoparticles concentrated overnight, reconstituted with various concentration of BSA (25° C.).
Figure 5B:
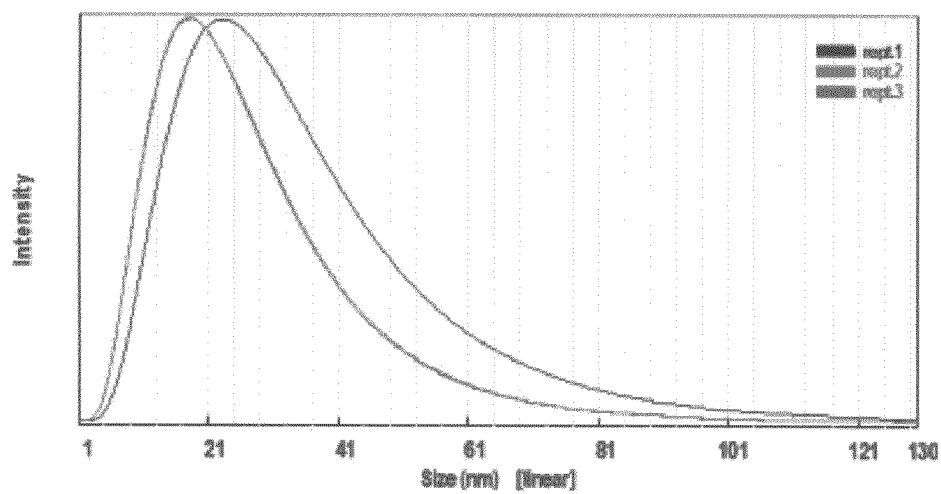
Figure 5C:
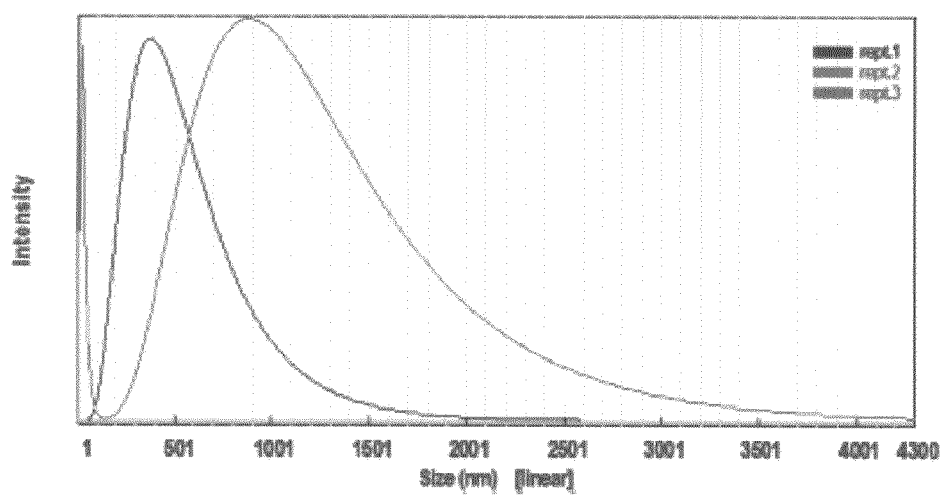
Figure 5D:
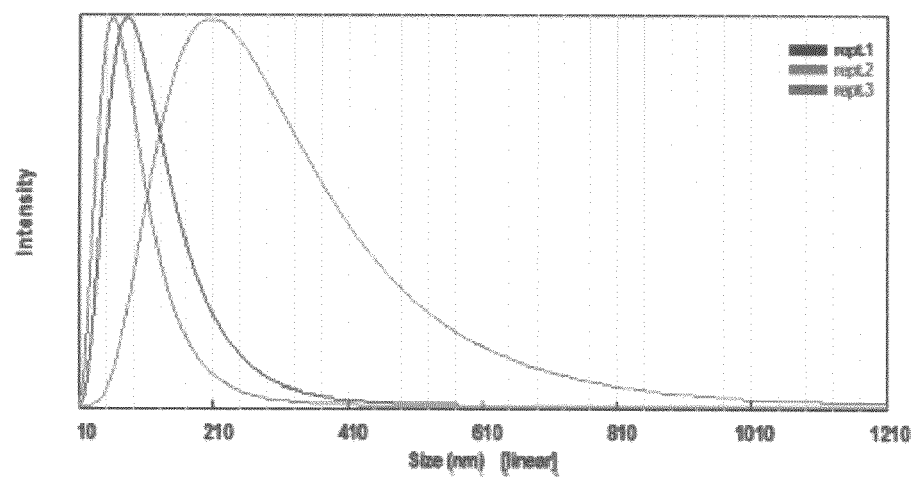
Figure 5E:
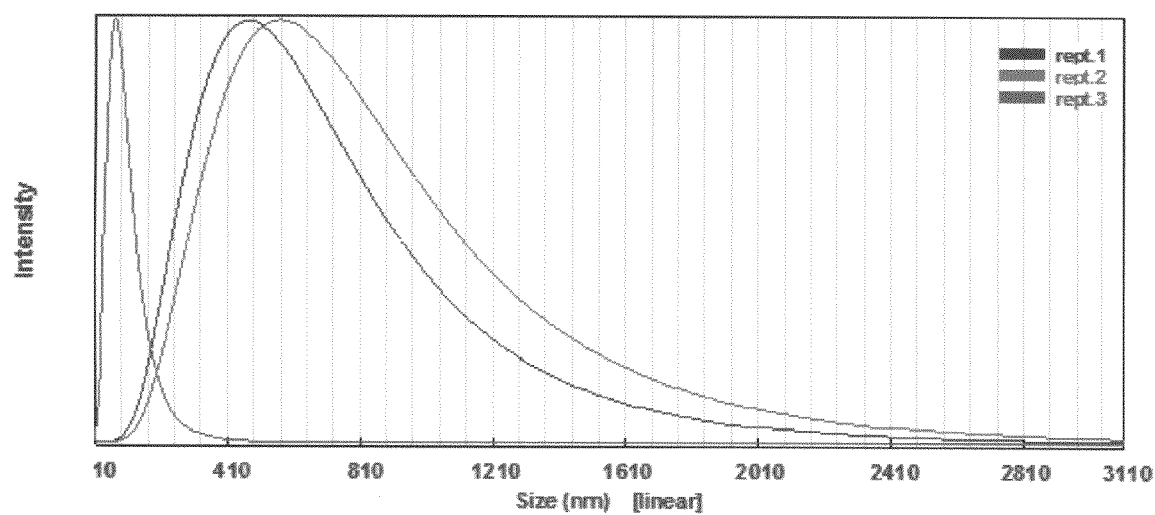
Figure 5F:
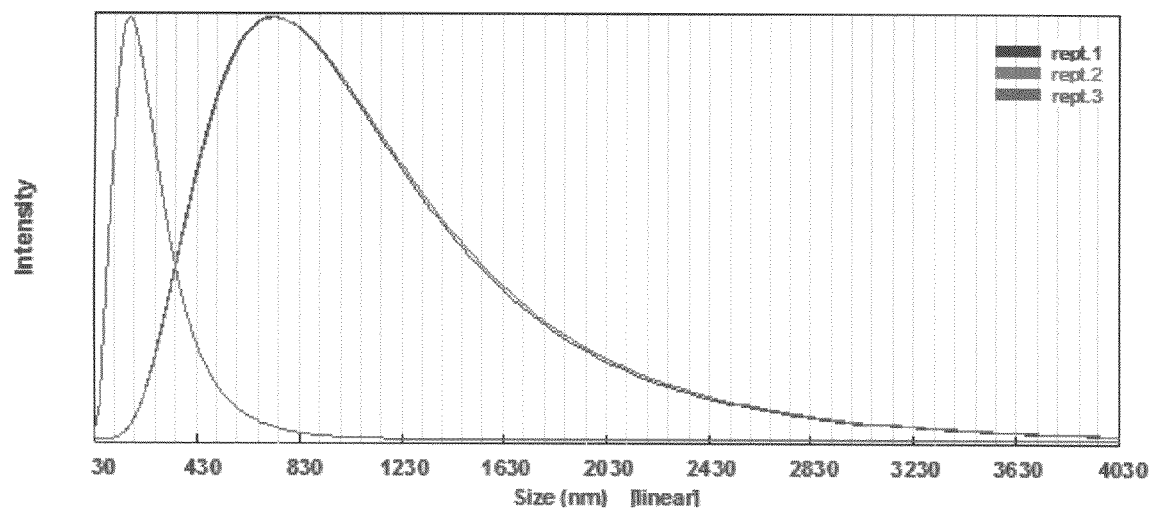
Figure 6A:
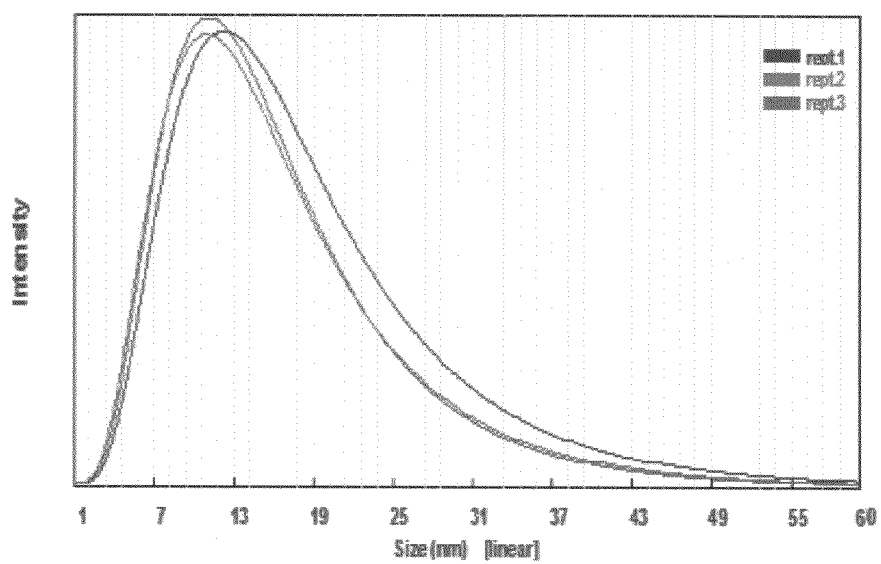
FIGS. 6A through 6D show the mean diameter (nm) of 25 µL Derinat DNA nanoparticles concentrated overnight with 500 µL of various concentrations of BSA, reconstituted with 1×PBS (37° C.).
Figure 6B:
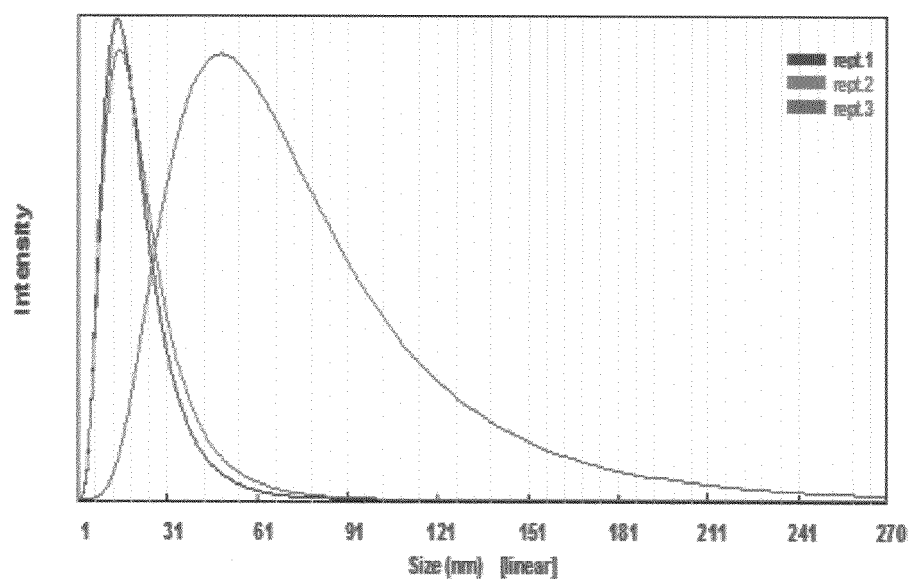
Figure 6C:
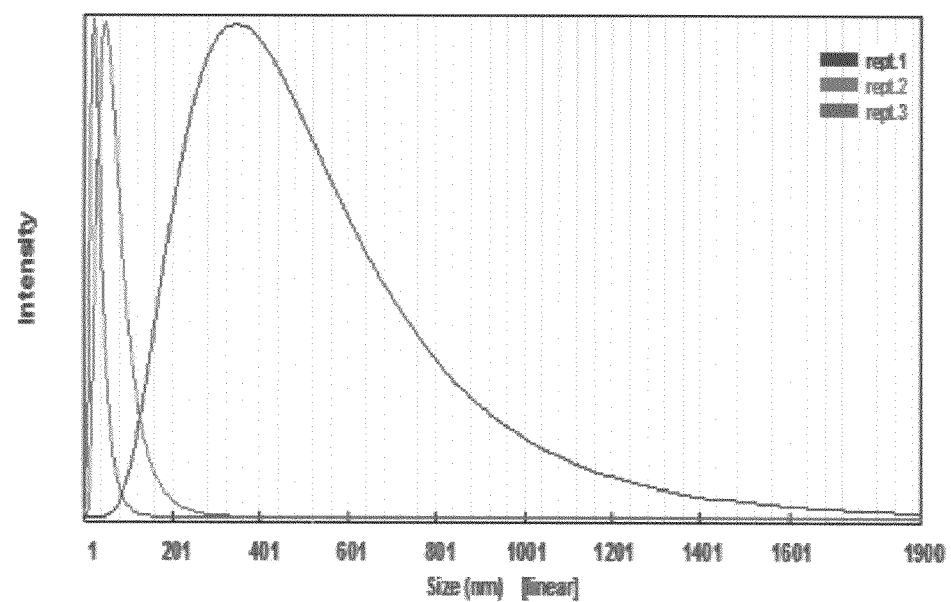
Figure 6D:
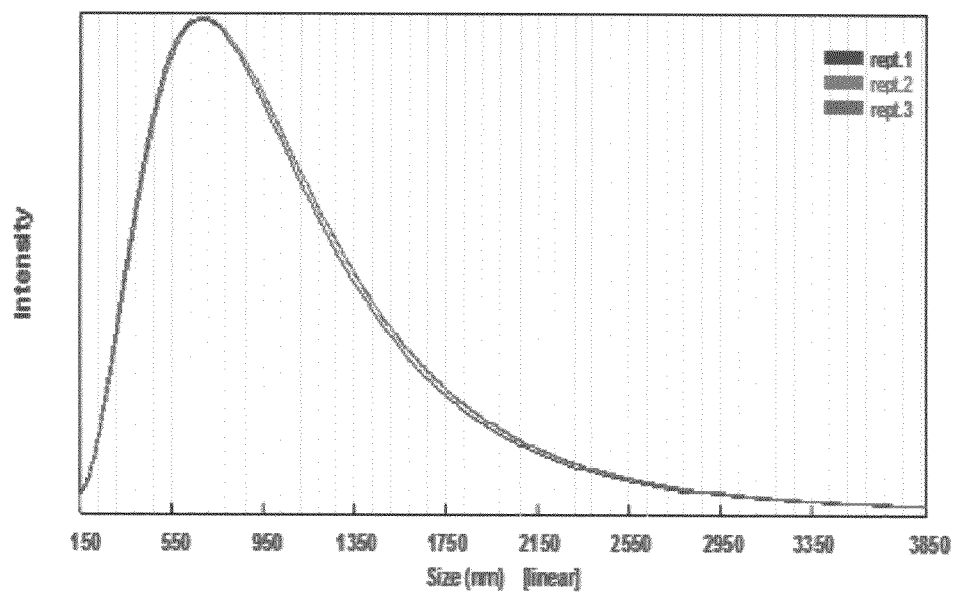

Analysis of the Sigma herring sperm ssDNA and Derinat by gel electrophoresis reveal that these two samples display similar characteristics (FIG. 2). Both show that a significant portion of the DNA is comprised of fragments between 1500 to less than 300 base pairs (exACTGene 1 kb DNA ladder was used). The size distribution obtained by the dynamic light scattering technique should be consistent with these results.

Analysis of the size distribution of concentrated DNA in a solution of bovine serum albumin (BSA), as measured by dynamic light scattering, indicates that the DNA display a significantly reduced mean diameter. A smaller diameter of the DNA nanoparticles enhances cellular uptake.

The size distribution of protein/DNA nanoparticles in solution is dependent on the concentration of BSA added. It was found that if BSA is used to reconstitute Sigma herring sperm DNA or Derinat, two different size distributions were observed—an indication that BSA is not tightly associated with DNA (FIGS. 7A and 7B). When either Derinat or Sigma herring sperm DNA was concentrated with BSA, however, a single, bell-shaped size distribution was observed. Derinat concentrated with 11.1 mg/mL BSA produces DNA nanoparticles with a mean diameter of 25.6±0.90 nm.

Heat also affects the size distribution of DNA nanoparticles in solution. Studies indicate that the size distribution of DNA nanoparticles in solution is not significantly altered when the temperature was raised from 25° C. to 37° C.

Discussion

Analysis of the size distribution of DNA nanoparticles in solution reveals that the mean diameter can be control by the addition or elimination of bovine serum albumin, where the addition of BSA (11.1 mg/mL) reduces the mean diameter of DNA nanoparticles by more than 90% of the mean diameter of the DNA polymer not associated with BSA.

Control of gene expression in a sequence-specific manner by silencing with siRNA in living cells holds great promise both as a novel therapeutic approach and as a new instrument for a drug target discovery. Cellular and animal models demonstrate the potential application of siRNA-based therapies for cancer, viral infections and inflammatory diseases. The stabilization of siRNA within a DNA nanoparticle opens an entirely novel practical avenue in the field of the delivery of gene therapeutic siRNAs, specifically RNAi silencing human or viral genes.

We claim:

1. A method of using a nanoparticle in a siRNA-based therapy, comprising administering a therapeutically effective amount of a-DNA nanoparticle-to a subject in need of a siRNA-based therapy, wherein said DNA nanoparticle comprises a DNA outer shell comprising one or more DNA polymers, and said DNA outer shell protects one or more siRNA molecules contained in the DNA nanoparticle.

2. A method of delivering a siRNA to a subject, comprising administering the siRNA to the subject, wherein the siRNA is contained in a DNA nanoparticle having a DNA outer shell.

3. The method of claim 2, wherein the DNA nanoparticle comprises protein.

4. The method of claim 3, wherein the protein is bovine serum albumin.

5. The method of claim 2, wherein the DNA nanoparticle comprises one or more DNA polymers derived from herring sperm DNA, salmon sperm DNA, human DNA, or Derinat.

6. The method of claim 2, wherein the DNA nanoparticle comprises a targeting molecule.

7. The method of claim 6, wherein the targeting molecule is an antibody or fragment thereof, or an aptamer.

8. A method of treating a disorder, comprising administering a DNA nanoparticle comprising a siRNA molecule that silences the expression of a target gene that causes the disorder, thereby treating the disorder, wherein said DNA nanoparticle has a DNA outer shell.

9. The method of claim 8, wherein the DNA nanoparticle further comprises a protein.

10. The method of claim 9, wherein the protein is bovine serum albumin.

11. The method of claim 8, wherein the nanoparticle comprises DNA from the group consisting of: one or more DNA polymers is herring sperm DNA, salmon sperm DNA, human DNA, or Derinat.

12. The method of claim 8, wherein the nanoparticle comprises a double-stranded RNA.

13. The method of claim 8, wherein the nanoparticle comprises a targeting molecule attached to the DNA polymer.

14. The method of claim 8, wherein the targeting molecule is an antibody or fragment thereof, or an aptamer.

* * * * *